United States Patent [19]

Task

[11] 4,343,539
[45] Aug. 10, 1982

[54] VIBRATION STABILIZED IMAGE PROJECTION SYSTEM

[75] Inventor: Harry L. Task, Dayton, Ohio

[73] Assignee: The United States of America as represented by the Secretary of the Air Force, Washington, D.C.

[21] Appl. No.: 240,048

[22] Filed: Mar. 3, 1981

[51] Int. Cl.³ .................. A61B 3/00; G03B 21/00; G03B 21/24

[52] U.S. Cl. .................... 353/122; 350/120; 351/17; 351/37; 351/38; 353/46; 353/69; 353/79; 353/121

[58] Field of Search .............. 351/17, 37, 38; 350/120; 353/46, 47, 48, 49, 50, 51, 69, 79, 121, 122

[56] References Cited

U.S. PATENT DOCUMENTS 3,125,927  3/1964  Erban ...................... 353/122
3,887,273  6/1975  Griffiths .................. 353/69

*Primary Examiner*—Steven L. Stephan
*Attorney, Agent, or Firm*—Donald J. Singer; John R. Flanagan

[57] ABSTRACT

A vibration stabilized image projection system includes a viewing screen supported on a vibratory platform, an image projector supported off the platform in a relatively vibration-free environment for projecting an image toward the screen, and an image stabilizing lens interposed between the projector and screeen for providing an optical link between them. The stabilizing lens is supported on the platform for undergoing vibratory movement therewith in X, Y and/or Z planes and relative to the projector. The lens focuses the image at a stationary position on the screen as the stabilizing lens, screen and platform undergo vibratory movement relative to the projector.

7 Claims, 3 Drawing Figures

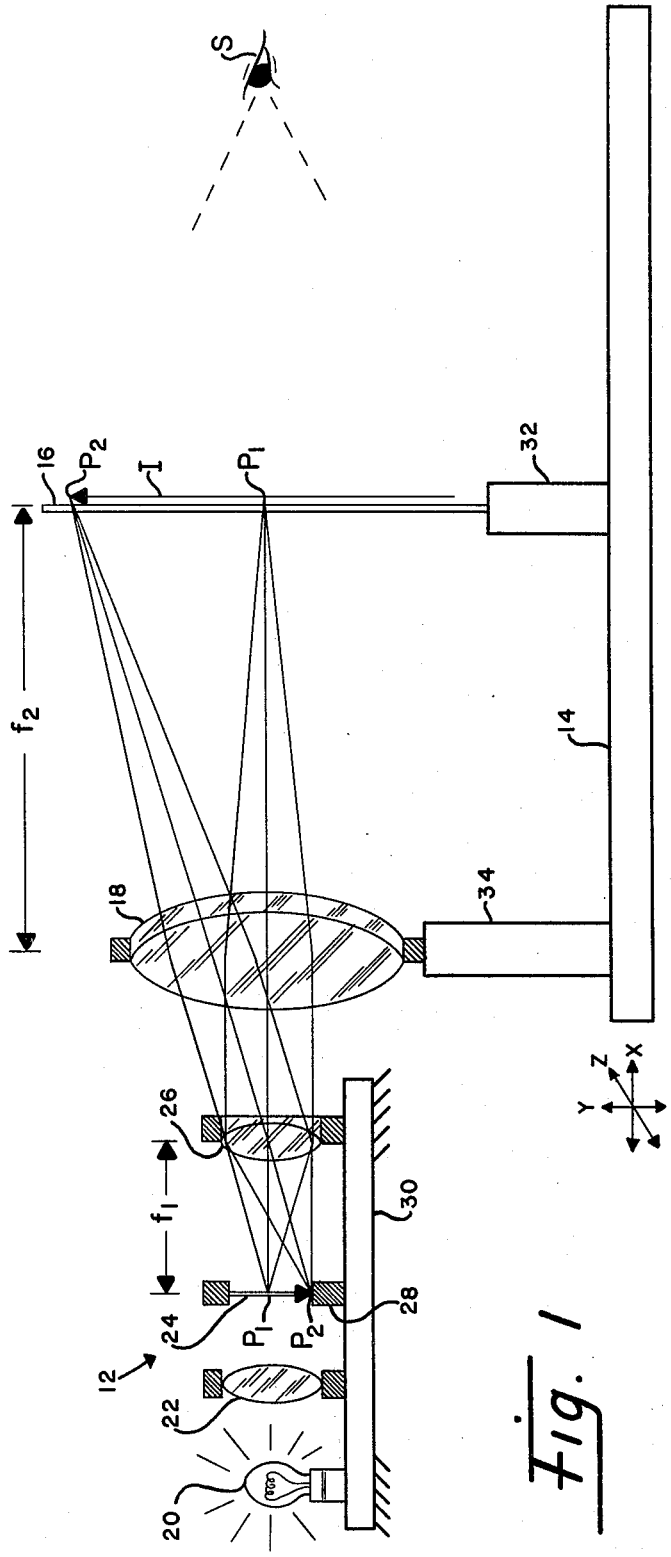
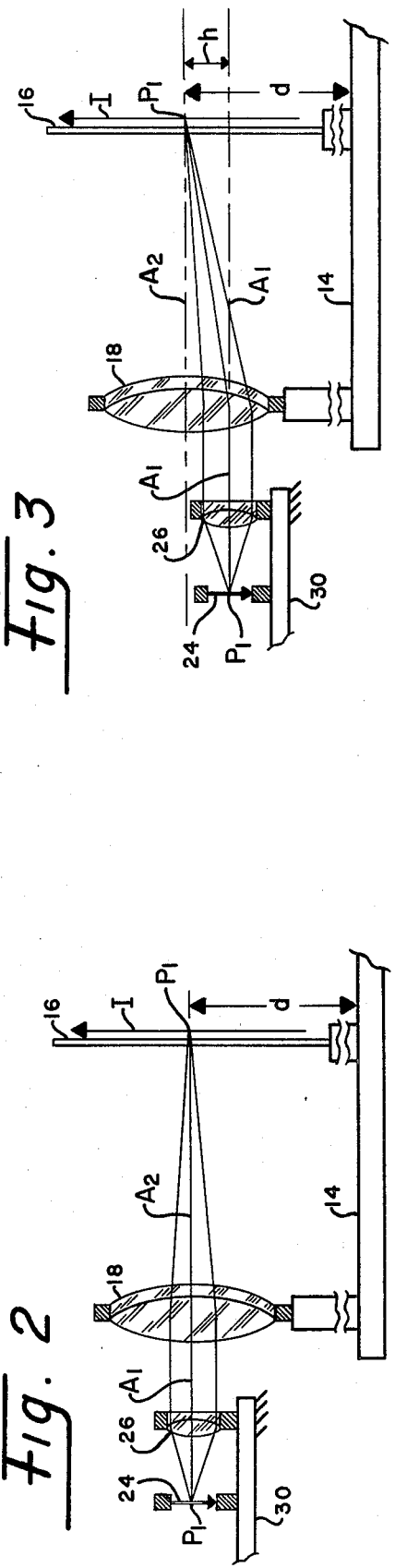
Fig. 1
Fig. 2
Fig. 3

VIBRATION STABILIZED IMAGE PROJECTION SYSTEM

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

The present invention broadly relates to image projection systems and, more particularly, is concerned with an optical arrangement for stabilizing the projection of an image on a viewing screen such that vibratory movement of a platform supporting the screen does not affect the position of the image with respect to the screen.

2. Description of the Prior Art

In conducting research on the effect of vibration on human vision, it has been the practice heretofore to place the image projector, viewing screen and the subject whose vision is being tested on a common vibratory platform. Such test setup was considered to be essential to produce test conditions which closely simulate the actual field environment.

One problem with this test setup has been the difficulty and high cost associated with providing an image projector that can withstand severe vibration while producing and maintaining an image at a stationary position on the screen as the screen undergoes vibration along with the platform and subject. Heretofore, mechanical solutions to this problem have been sought, being primarily directed along the lines of providing some type of vibration damping means for protecting the components of the image projector. However, these approaches have not met with significant success, and so a need still exists for a more practical and cost effective solution.

SUMMARY OF THE INVENTION

The present invention obviates the need for an image projector having a mechanical design which can withstand severe vibration. The need for a mechanical solution has been eliminated by simply removing the image projector from the vibratory platform and interposing an optical link between the projector and the viewing screen. Therefore, the solution achieved by the present invention is optical rather than mechanical.

The present invention recognizes that the placing of the image projector on the vibratory platform was the real problem in the prior art approach and not the lack of a projector design adequate to withstand vibration. This recognition coupled with the inside necessary to attempt an optical approach paved the way to the solution proposed by the present invention whose elegance is augmented rather than dimished by its simplicity, low cost and reliability.

Accordingly, the present invention provides an image projection system, which comprises: (a) a platform subject to vibratory movement in X, Y and/or Z planes; (b) an image viewing screen supported on the platform for undergoing vibratory movement therewith; (c) an image projector supported off the platform in a relatively vibration-free environment for projecting an image toward the viewing screen; and (d) an image stabilizing lens interposed between the projector and the viewing screen and supported on the platform for undergoing vibratory movement therewith and relative to the image projector. The image stabilizing lens receives the collimated image from the projector and focuses the image at a given position on the screen when the platform is at rest and maintains the focus of the image at the same position on the screen during vibratory movement with the platform and screen.

BRIEF DESCRIPTION OF THE DRAWINGS

FIG. 1 is a schematical representation of the vibration stabilized image projection system of the present invention.

FIG. 2 schematically depicts the optical link provided between the image projector and viewing screen by the image stabilizing lens when the optical axes of the projector and stabilizing lens are coaxially aligned.

FIG. 3 schematically depicts the optical link provided between the projector and screen by the stabilizing lens when the optical axes of the projector and stabilizing lens are laterally offset or displaced from one another.

DETAILED DESCRIPTION OF THE INVENTION

Referring to the drawings, and particularly to FIG. 1, there is shown schematically the preferred embodiment of the vibration stabilized image projection system of the present invention, being generally designated 10. The image projection system 10 includes an image projector 12, a X-Y-Z vibratory platform 14, and a viewing screen 16 and a stabilizing lens 18, both of which are supported on the platform 14 for vibratory movement therewith. The image projector 12 is supported adjacent one end of, but off, the platform 14 in a relatively vibration-free environment. A subject S whose vision is to be tested under vibratory conditions would be seated at the end of the platform opposite to the one adjacent the projector 12 for viewing the screen 16, which preferably is of the rear projection type.

The image projector 12 of the system 10 includes a light source in the form of projection lamp 20 which radiates incoherent light upon a condensing lens 22. The condensed beam of light from lens 22 is directed through a transparent target slide 24 disposed in the object plane of the projector 12 between the condensing lens 22 and an objective lens 26. The objective lens 26 is located one focal length, $f_1$, from the target slide 24 to project the image of the target slide to optical infinity.

Being supported on the end of the platform 14 adjacent to the projector 12, the image stabilizing lens 18 is interposed between the objective lens 26 of the projector 12 and the viewing screen 16. The stabilizing lens 18 is located at one focal length, $f_2$, from the screen 16 on the side thereof opposite from the subject S. The lens 18 receives the collimated image from the objective lens 26 and focuses the image at I on the rear projection viewing screen 16. In FIG. 1, there is shown the bundles of parallel rays originating from points $P_1$ and $P_2$ in the object of target slide 24 and refocused in the conjugate image points $P'_1$ and $P'_2$ on the screen 16. The image size is $f_2$ divided by $f_1$ times larger than the size of the object on target slide 24. It should be noted that the stabilizing lens 18 is of substantially larger size in diameter than the objective lens 26 so that the collimated image from the objective lens will always be received on some portion of the stabilizing lens as the latter undergoes lateral movement with the platform relative to the projector.

As seen in FIG. 1, the projection lamp 20, condensing lens 22, objective lens 26, and a holder 28 for supporting the target slide 24 are all mounted on a base 30 of the projector 12 which is stationarily supported off the platform 14 in a relatively vibrationfree environment. The viewing screen 16 and image stabilizing lens 18 are securely mounted to the vibratory platform 14 by respective support frames 32 and 34 for movement with the platform 14 in orthogonal X, Y and/or Z planes.

FIGS. 2 and 3 illustrate the optical link or couple provided by the image stabilizing lens 18 between the screen 16 and the objective lens 26 for maintaining the projected image at a stationary position on the screen 16 even as the screen and stabilizing lens undergo vibratory movement with the platform 14.

In FIG. 2, the platform 14 is seen either at rest or at the mid-point of its vibratory movement. Regardless of which, the optical axis $A_2$ of the stabilizing lens 18 and image on the screen 16 is coaxially aligned with the optical axis $A_1$ of the projector 12. The light rays leaving from any particular point, such as center point $P_1$, in the object of target slide 24 are made parallel by the objective lens 26. The image stabilizing lens 18, in turn, takes each bundle of parallel rays and focuses it to the conjugate point $P_1'$ in the image on the screen 16.

In FIG. 3, upward lateral movement of the platform 14 has now displaced the optical axis $A_2$ of the stabilizing lens 18 above the axis $A_1$ of the projector 12. The bundle of parallel rays originating from point $P_1$ are now refocused by stabilizing lens 18 to maintain the conjugate image point $P_1'$ at the same stationary position on the screen 16, which moves with the lens 18 and platform 14 relative to the projector 12. For instance, the center point $P_1$ of the object on target slide 24 is imaged at the same point $P_1'$ on the screen 16, located at a distance d above the platform 14, even though the platform has moved relative to the projector 12 such that optical axis $A_2$ of the stabilizing lens 18 is displaced at distance h from the optical axis $A_1$ of the projector. The same stability of image points hold for all points of the object on target slide 24.

Consequently, the position of the image on the screen 16 with respect to the vibrating platform 14 is independent of lateral movement of the platform in X-Y-Z planes. Furthermore, any lateral movement of the platform 14 does not affect the position of the image with respect to the subject S who is also on the platform.

Having thus described the invention, what is claimed is:

1. A vibration stabilized image projection system, comprising:
   (a) a platform subject to vibratory movement in X, Y and/or Z planes;
   (b) an image viewing screen supported on said platform for undergoing vibratory movement therewith;
   (c) an image projector supported off said platform in a relatively vibration-free environment for projecting an image toward said screen; and
   (d) an image stabilizing lens interposed between said projector and screen for providing an optical link between them, said stabilizing lens being supported on said platform for undergoing vibratory movement therewith and relative to said projector, said lens focusing said image from said projector at a stationary position on said screen as said lens, screen and platform undergo vibratory movement relative to said projector.

2. The image projection system as recited in claim 1, wherein said projector includes an objective lens for projecting said image in a collimated image which is received by said stabilizing lens.

3. The image projection system as recited in claim 2, wherein said stabilizing lens is of substantially larger size in diameter than said objective lens so that said collimated image from said objective lens will always be received on some portion of said stabilizing lens as the latter undergoes movement with said platform relative to said projector.

4. A vibration stabilized image projection system, comprising:
   (a) a platform subject to vibratory movement in X, Y and/or Z planes;
   (b) an image viewing screen supported on said platform for undergoing vibratory movement therewith;
   (c) an image projector supported off said platform in a relatively vibration-free environment for projecting an image to optical infinity in a collimated image toward said viewing screen; and
   (d) an image stabilizing lens interposed between said projector and said viewing screen and supporting on said platform for undergoing vibratory movement therewith and relative to said projector, said stabilizing lens receiving said collimated image from said projector and focusing the image at a stationary position on said screen when said platform is at rest and maintaining the image at the same stationary position on said screen as said stabilizing lens, screen and platform undergo vibratory movement relative to said projector.

5. The image projection system as recited in claim 4, wherein said projector has a first optical axis which is substantially coaxial with a second optical axis of said stabilizing lens and the image on said screen when said platform is at rest, said second optical axis undergoing displacement relative to said first axis when said platform undergoes vibratory movement.

6. The image projection system as recited in claim 4, wherein said projector includes an objective lens for projecting the collimated image received by said stabilizing lens.

7. The image projection system as recited in claim 6, wherein said stabilizing lens is of substantially larger size in diameter than said objective lens so that said collimated image from said objective lens will always be received on some portion of said stabilizing lens as the latter undergoes movement with said platform relative to said projector.

* * * * *

UNITED STATES PATENT AND TRADEMARK OFFICE
CERTIFICATE OF CORRECTION

PATENT NO. : 4,343,539
DATED : August 10, 1982
INVENTOR(S) : Harry L. Task

It is certified that error appears in the above—identified patent and that said Letters Patent is hereby corrected as shown below:

Col 1, line 55, delete "inside" and insert --- insight ---.

Col 4, line 33 (claim 4, part d), delete "supporting" and insert --- supported ---.

*Signed and Sealed this*

*Sixteenth* Day of *November 1982*

[SEAL]

*Attest:*

GERALD J. MOSSINGHOFF

*Attesting Officer* *Commissioner of Patents and Trademarks*